United States Patent [19]

Shemano

[11] E Patent Number: Re. 32,145

[45] Reissued Date of Patent: May 13, 1986

[54] ORALLY ACTIVE TOLCICLATE [(AND TOLNAFTATE)]

[75] Inventor: Irving Shemano, Columbus, Ohio

[73] Assignee: Hercules Incorporated, Wilmington, Del.

[21] Appl. No.: 668,452

[22] Filed: Nov. 5, 1984

Related U.S. Patent Documents

Reissue of:

[64] Patent No.: 4,348,407
Issued: Sep. 7, 1982
Appl. No.: 258,830
Filed: Apr. 29, 1981

[51] Int. Cl.[4] ..... A61K 31/27
[52] U.S. Cl. ..... 514/481; 514/480
[58] Field of Search ..... 514/481, 480

[56] References Cited

U.S. PATENT DOCUMENTS 3,855,263 12/1974 Melloni et al. ..... 424/300

OTHER PUBLICATIONS

Noguchi et al, Yakugaku Zasshi (J. Pharmaceutical Society of Japan), vol. 88, No. 3, pp. 353–358 (Mar. 1968).

The Merck Index, 9th Ed., Merck & Co. Inc., Rahway, N.J., 1976, p. 1224.

Noguchi et al, Antimicrobial Agents and Chemotherapy 1962, (May, 1963) pp. 259–267.

*Primary Examiner*—Jerome D. Goldberg
*Attorney, Agent, or Firm*—Marion C. Staves

[57] ABSTRACT

It has been found that fungal diseases can be effectively treated systemically by oral administration of tolciclate [or tolnaftate]. The [drugs] *drug* will generally be administered in divided daily doses in the form of tablets, capsules, syrups or suspensions.

5 Claims, No Drawings

ORALLY ACTIVE TOLCICLATE [(AND TOLNAFTATE)]

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to treating fungal diseases. More particularly, this invention relates to the systemic treatment of fungal diseases by oral administration of [an antifungal agent selected from] tolciclate [and tolnaftate] and to medicaments containing said [agents] *agent* for oral administration.

2. Description of the Prior Art

The human body is subject to many fungal infections, some of which have been a problem to man since before recorded history. Modern science has been successful in treating many fungal diseases. The most success has occurred in the topical treatment on exposed areas of the body. Numerous compounds are known to be effective in such topical treatment. However, not all fungal infections occur in exposed areas and are thus not amenable to topical treatment. Some fungal diseases occur internally or deep in the dermal layer of the skin or in unexposed areas, such as under fingernails, and can only be treated systemically. Unfortunately, only a few antifungal agents are known to be systemically effective when administered orally. One of the most widely prescribed drugs for the systemic treatment of fungal diseases is griseofulvin. Since the chronic feeding of this drug to mice results in their developing liver tumors, its use is not justified in minor or trivial infections. Accordingly, there is great interest in finding antifungal agents which can be effectively and safely administered orally.

Tolciclate [and tolnaftate are] *is a* known antifungal [agents] *agent* effective in topical treatment of fungal diseases. Tolciclate, i.e., O-(1,4-methano-1,2,3,4-tetrahydro-6-naphthyl)N-methyl-N-(m-tolyl)-thiocarbamate having the formula

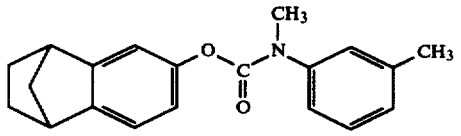

is described in U.S. Pat. No. 3,855,263. The patent indicates that the compound has antifungal activity when applied topically. [Tolnaftate, i.e., methyl-(3-methylphenyl)carbamothioic acid O-2-naphthalenyl ester having the formula

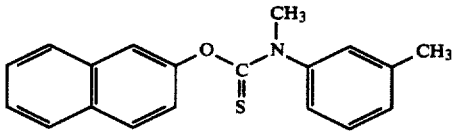

is described in U.S. Pat. No. 3,334,126. This patent indicates that tolnaftate has antifungal activity when applied topically.] All indications have been that tolciclate [and tolnaftate are] *is* only effective in topical treatment of fungal disease. [In fact, T. Noguchi et al, in an article entitled "Antitrichophyton Activity of Naphthiomates", on pages 259–267 of Antimicrobial Agents and Chemotherapy (1962), states (page 265) that tolnaftate was found to be "totally ineffective by oral and parenteral administration" against fungal disease and "only griseofulvin was effective". In a subsequent article entitled "Antifungal Properties of Tolnaftate In Vitro and In Vivo", by M. J. Weinstein et al, on pages 595–601 of Antimicrobial Agents and Chemotherapy (1965), the following statement appears, "Tolnaftate was found to be active only by topical application and inactive by the oral and intraperitoneal routes of administration" (bottom of page 597 to top of page 598).]

SUMMARY OF THE INVENTION

It has now surprisingly been found that tolciclate [and tolnaftate] can be administered orally in divided daily doses to effectively combat fungal diseases. Accordingly this invention relates to (1) the method of treating fungal diseases which comprises orally administering to a person suffering therefrom a therapeutic amount of [antifungal agent selected from] tolciclate [and tolnaftate] and (2) an antifungal medicament for oral administration comprising:

a. from about 10% to about 90% by weight of an [antifungal agent selected from] tolciclate and [tolnaftate.]

b. from about 90% to 10% by weight of a pharmaceutically acceptable carrier.

Unlike some antifungal agents, the orally administered [agents] *agent* of this invention [are] *is* relatively nontoxic. For example, when administered orally to rats, tolciclate was found to have an $LD_{50}$ of greater than 4000 mg/kg. By the term "$LD_{50}$" is meant lethal dose to 50% of the animals being tested. [Tolnaftate administered orally to rats was found to have an $LD_{50}$ of greater than 5000 mg/kg.]

The [agents] *agent* of this invention [are] *is* effective against a wide spectrum of fungal diseases. Typical fungus infections which can be treated systemically according to the process of this invention are ringworm infections of the skin, hair and nails, namely tinea corporis, tinea pedis, tinea cruris, tinea barbae, tinea capitis, tinea unguium and tinea versicolor when caused by organisms such as Microspora, Trichophyta, Epidermophyton floccosums, and Pityrospora, i.e. P. obiculare and P. ovale.

Oral dosages in the order of 1 to 50 mg/kg, most preferably 5 to 25 mg/kg daily of the agents [are] *is* highly effective in suppressing fungal diseases. Most preferably the [agents] *agent* will be administered in divided daily doses. The specific dosage will depend upon the site of the infection, type of fungus, and duration of treatment. Any pharmaceutical composition for oral administration containing the [agents] *agent* can be used in the process of this invention. In general, however, the [agents] *agent* will be administered in the form of tablets, capsules, syrups or suspensions.

Typical dosage forms are as follows:

A. The following ingredients are mixed in a blender for 5 minutes and then compressed into 200 mg. tablets:

| Ingredients | Grams per 1000 tablets |
|---|---|
| Tolciclate | 100 g. |
| Lactose, USP | 50 g. |
| Microcrystalline Cellulose, USP | 49 g. |

-continued

| Ingredients | Grams per 1000 tablets |
|---|---|
| Magnesium Stearate, USP | 1 g. |

[B. The following ingredients are mixed in a blender for 5 minutes and then 250 mg. portions are filled into hard gelatin capsules:

| Ingredients | Grams per 1000 capsules |
|---|---|
| Tolnaftate | 100 g. |
| Lactose, USP | 100 g. |
| Starch, USP | 48 g. |
| Magnesium Stearate, USP | 2 g.] |

[C.] *B.* The following ingredients are utilized in forming a suspension:

| Ingredients | Per 10 liters |
|---|---|
| Tolciclate | 100 g. |
| Cellulose gum 7MF | 80 g. |
| Veegum | 100 g. |
| Sucrose, USP | 1500 g. |
| Alcohol, USP | 500 ml. |
| Methylparaben, USP | 20 g. |
| Propylparaben, USP | 5 g. |
| Vanillin, USP | 0.5 mg. |
| Alva Cherry V-41 | 50 ml. |
| D&C Red No. 33 | 0.7 g. |
| Adipic Acid, FCC (qs pH 5–6) | 7 g. |
| Purified water, USP qs | 10 liters |

The gums are dispersed in about ½ the volume of water heated to 70° C. and then cooled to 35° C. The sucrose and D&C Red dye are dissolved in a small volume of the water and added to the gum dispersion. Next, the tolciclate is dispersed in water and added to the gum dispersion. The parabens, vanillin and Alva Cherry flavoring are dissolved in alcohol and added to the dispersion. A quantity (7 grams) of adipic acid sufficient to adjust the pH to between 5 and 6 is added and finally the volume is adjusted to 10 liters with purified water.

Various other dosage forms will be obvious to those skilled in the art, including sustained release formulations and formulations containing other medicinal agents such as analgesics, antibiotics, etc.

The following examples are presented to illustrate the process of this invention.

EXAMPLE 1

This example illustrates the absorption of tolciclate after oral administration and its migration to the skin.

Fifteen male, Swiss-Webster mice weighing 25–30 g were divided into groups of three. All animals were fasted overnight prior to the experiment. Food was allowed 8 hours after dosing.

$^{14}$C-tolciclate, O-(1,4-methano-1,2,3,4-tetrahydro-6-naphthyl)N-methyl-N-m-tolyl[methyl-$^{14}$C]thiocarbamate, was prepared at a specific activity of 7.48μ Ci/mg. Powdered $^{14}$C-tolciclate was suspended in 0.25% aqueous solution of methylcellulose at a concentration of 0.5 mg/ml. Each animal was gavaged with 10 mg/ml of suspension, resulting in a 5 mg/kg dose.

Blood samples were taken at 0.5, 1, 2, 4, 8, 12, 48 and 72 hours after the dose of $^{14}$C-tolciclate. At 4 hours post-dose, 3 animals were killed and the liver, kidney, lung, skin, heart, spleen and brain tissues were removed. This procedure was repeated with 3 animals at 8, 24 and 72 hours. An estimation of biliary excretion was obtained by giving an intraperitoneal injection of 5 mg/kg of $^{14}$C-tolciclate to 2 mice and following fecal elimination over a 72 hour period. Another group of 3 mice received a daily oral dose of 5 mg/kg of $^{14}$C-tolciclate for 8 days. Blood was taken at 1, 5 and 8 days. The same tissues listed above were taken from this group on day 8.

All of the materials collected from the mice were assayed for $^{14}$C by liquid scintillation counting on a Packard 2425 scintillation counter. Solid material was combusted using a Packard 306 Sample oxidizer prior to liquid scintillation counting. Samples of the skin and lyophilized urine were extracted with methanol and samples of the blood were extracted with ethyl acetate and the extracts analyzed by thin layer chromatography. Analysis of fecal and urine data following the single 5 mg/kg dose showed that at least 70% of the tolciclate administered orally to the mice was absorbed. The absorption appeared to be rapid with a peak level in the blood during the first hour or two. The major route of elimination was biliary, while about 25% of the dose was excreted via the urine. The drug was extensively metabolized, unchanged tolciclate was not found in the urine and only minute amounts were present in the blood. However, the major compound, identified by chromatography, in the skin was unmetabolized tolciclate. Based on the analysis, tolciclate levels in the skin ranged from 147–180 ng/g 4 hours after oral administration—this is a concentration that has been shown effective in in vitro antifungal testing.

The blood concentration of $^{14}$C-tolciclate in the mice following oral administration is shown in Table 1 below.

TABLE 1

| Time (hours) | Tolciclate Equivalent (ng/g) |
|---|---|
| 0.5 | 469.5 ± 46.9 |
| 1.0 | 618.1 ± 59.4 |
| 2.0 | 364.5 ± 57.9 |
| 4.0 | 229.3 ± 20.5 |
| 8.0 | 210.0 ± 8.1 |
| 24.0 | 72.5 ± 6.2 |
| 48.0 | 60.3 ± 13.2 |
| 72.0 | 48.8 ± 10.6 |

The concentration of tolciclate in the skin of the mice following a single oral dose (μg/g wet tissue) is given in Table 2.

TABLE 2

| Hours | Concentration* |
|---|---|
| 4 | 0.21 ± 0.04 |
| 8 | 0.16 ± 0.01 |
| 24 | 0.11 ± 0.02 |
| 72 | 0.03 ± 0.00 |

*The data are given as tolciclate equivalents in mean ± SEM (n = 3).

The concentration of tolciclate in the tissue of the mice following eight oral daily doses is given in Table 3.

TABLE 3

| Tissue | g/g wet tissue* |
|---|---|
| Liver | 1.25 ± 0.12 |
| Kidney | 0.41 ± 0.05 |
| Lung | 0.22 ± 0.02 |
| Skin | 0.13 ± 0.02 |
| Heart | 0.07 ± 0.01 |
| Spleen | 0.06 ± 0.00 |

TABLE 3-continued

| Tissue | g/g wet tissue* |
|---|---|
| Brain | 0.03 ± 0.00 |

*Tissues were taken 24 hours after the last dose. The data are given as tolciclate equivalent in mean ± SEM (n = 3).

EXAMPLE 2

This example illustrates the effectiveness of tolciclate, [tolnaftate] and griseofulvin as antifungal agents when administered orally.

[Four] *Three* groups of albino guinea pigs were observed for two weeks to make sure they were disease free. Following the observation period they were dosed according to the following regimen: One group (the control) was gavaged twice a day for 10 days with a 0.25% aqueous methylcellulose solution. The second group was gavaged twice a day for 10 days with 50 mg/kg of tolciclate suspended in a 0.25% aqueous solution of methylcellulose. The third group was gavaged twice a day for 10 days with 50 mg/kg of [tolnaftate suspended in a 0.25% aqueous solution of methylcellulose. The fourth group was gavaged twice a day for 10 days with 50 mg/kg of] griseofulvin in the form of a commercial elixir ("Grifulvin V" sold by Ortho Pharmaceutical Corp.).

On the fifth day of treatment all of the animals were infected with T. mentagrophytes "1782" fungus by the following method: An area of several centimeters on the back of each guinea pig was shaved free of hair, abraded and inoculated with a suspension of a culture of T. mentagrophytes suspended in physiological saline solution. The resulting skin lesions were checked on day 7, 10 and 15 after inoculation and the size of the lesions measured. On days 10 and 15 clinical infections i.e., grossly observable skin lesions, were observed in fourteen out of the fourteen controls, seven out of the fifteen tolciclate treated animals, [twelve out of the twenty tolnaftate treated animals] and four out of the nineteen griseofulvin treated animals. The average size of the infection site and the day it was measured are tabulated in Table 4.

TABLE 4

| Treatment | Day | Size of infection site, $cm^2$ |
|---|---|---|
| Control | 10 | 8.5 |
| | 15 | 6.7 |
| Tolciclate | 10 | 0.03 |
| | 15 | 0.09 |
| [Tolnaftate | 10 | 0.025 |
| | 15 | 0.1] |
| Griseofulvin | 10 | 0 |
| | 15 | 0.09 |

On day 10 after inoculation with T. mentagrophytes each animal was tested for the presence of fungus as described in Manual, Chemical Microbiology, 2nd Edition, Lenette, Spaulding and Truant. American Society of Microbiology, 1974, pp. 945–946. Thirteen out of the fourteen controls tested positive, indicating fungus infection on day 10. All of the treated animals were negative.

What we claim and desire to protect by Letters Patent is:

1. A process of suppressing fungal disease which comprises orally administering to a person infected therewith a therapeutically effective amount for antifungal purposes of [an antifungal agent selected from the group consisting of] tolciclate [and tolnaftate].

2. The process of claim 1 where the [antifungal agent] *tolciclate* is administered in the form of a tablet.

3. The process of claim 1 where the [antifungal agent] *tolciclate* is administered in the form of a capsule.

4. The process of claim 1 wherein the [antifungal agent] *tolciclate* is administered in the form of a liquid suspension.

5. The process of claim 1 wherein the [antifungal agent] *tolciclate* is administered in divided daily doses.

[6. the process of claim 1 where the antifungal agent is tolciclate.]

[7. The process of claim 1 where the antifungal agent is tolnaftate.]

* * * * *

UNITED STATES PATENT AND TRADEMARK OFFICE

CERTIFICATE OF CORRECTION

PATENT NO. : Re. 32,145

DATED : May 13, 1986

INVENTOR(S) : Irving Shemano

It is certified that error appears in the above-identified patent and that said Letters Patent is hereby corrected as shown below:

On the title page assignee should read

--(73) Assignee: Adria Laboratories, Inc. --.

Signed and Sealed this

Fourteenth Day of October, 1986

[SEAL]

*Attest:*

DONALD J. QUIGG

*Attesting Officer*

*Commissioner of Patents and Trademarks*